United States Patent [19]

Golay

[11] Patent Number: 4,475,249
[45] Date of Patent: Oct. 9, 1984

[54] AIR CLEANING MAGNETIC ATTACHMENT FOR A WELDER'S FACE MASK

[76] Inventor: Kenneth W. Golay, P.O. Box 423, Ardmore, Okla. 73401

[21] Appl. No.: 422,428

[22] Filed: Sep. 23, 1982

[51] Int. Cl.³ .......................... A42B 1/00; A61F 9/00
[52] U.S. Cl. .................................................. 2/8; 2/7; 2/11; 2/427; 2/429; 2/438
[58] Field of Search ..................... 2/7, 8, 429, 11, 427, 2/438

[56] References Cited

U.S. PATENT DOCUMENTS

| D. 226,251 | 2/1973 | Raschke | 2/7 |
|---|---|---|---|
| 233,891 | 11/1880 | Stoddard | 209/215 |
| 1,205,834 | 11/1916 | Yovich | 2/7 |
| 1,658,335 | 2/1928 | Huntsman | 2/8 |
| 2,911,038 | 11/1959 | Prommelt | 2/8 |
| 3,678,929 | 7/1972 | Buscher | 2/427 |
| 3,720,956 | 3/1973 | Raschke | 2/8 |
| 4,180,868 | 1/1980 | Snow | 2/7 |
| 4,422,185 | 12/1983 | Cook | 2/8 |

Primary Examiner—Werner H. Schroeder
Assistant Examiner—Mary A. Ellis
Attorney, Agent, or Firm—Robert K. Rhea

[57] ABSTRACT

A section of flexible magnetic sheet material is bonded to the inner surface of a welder's face mask in that area below and on either side of an eye protective lens covered opening of a welder's face mask.

3 Claims, 3 Drawing Figures

AIR CLEANING MAGNETIC ATTACHMENT FOR A WELDER'S FACE MASK

BACKGROUND OF THE INVENTION

1. Field of the Invention

The present invention relates to welder's eye shields and face masks and more particularly to a magnetic attachment therefor for protecting the lungs from inhalation of minute metallic particles.

Welder's eye shields and face masks presently in use comprise a panel portion extending at least the full length of the welder's face with the panel having a lens covered opening for shielding the eyes from infrared and ultraviolet rays generated by the welding action. Side members, integrally connected with the face panel, are pivotally connected to opposing sides of a headgear supporting the face mask on the welder's head in a manner to easily pivot the face mask from a face shielding position to an upward out-of-the-way position for inspecting the work before and after the welding action. The face mask is normally maintained in close spaced relation with respect to the welder's nose and mouth but does not have provision for preventing inhalation of air entrained metallic particles in the air breathed by the welder during a welding operation.

2. Description of the Prior Art

The most pertinent prior patent is believed U.S. Pat. No. 233,891 which discloses an earpiece supported nose guard bridging the wearer's nose and provided with downwardly open sockets on either side thereof which receive a permanent magnet bar for attracting airborne metallic particles and preventing inhalation of steel filings, or the like.

This invention is believed distinctive over this patent by providing a section of magnetic flexible sheet material which is bonded to the inner surface of a welder's eye shield and face mask for attracting minute airborne metallic particles.

SUMMARY OF THE INVENTION

A generally rectangular section of flexible sheet material, having magnetic properties, is dimensioned to span the inner surface of the face shielding portion of a welder's mask. The section of sheet material is provided with a substantially U-shaped opening in one of its ends and is bonded by adhesive to the inner surface of a welder's face mask with the U-shaped end portion surrounding three sides of the lens covered opening.

The principal object is to provide a lung protector for a welder's face mask in which a sheet of flexible magnetic material is bonded to the inner surface of the face mask for magnetically attracting airborne metallic particles and thus clean the air breathed by the welder.

DESCRIPTION OF THE PREFERRED EMBODIMENT

Figure 1:
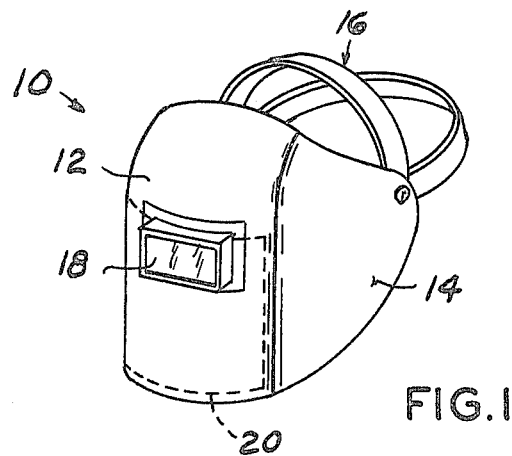
FIG. 1 is a perspective view of a substantially conventional welder's eye shield and face mask illustrating, by dotted lines, the relative position of the device when installed thereon.
Figure 2:
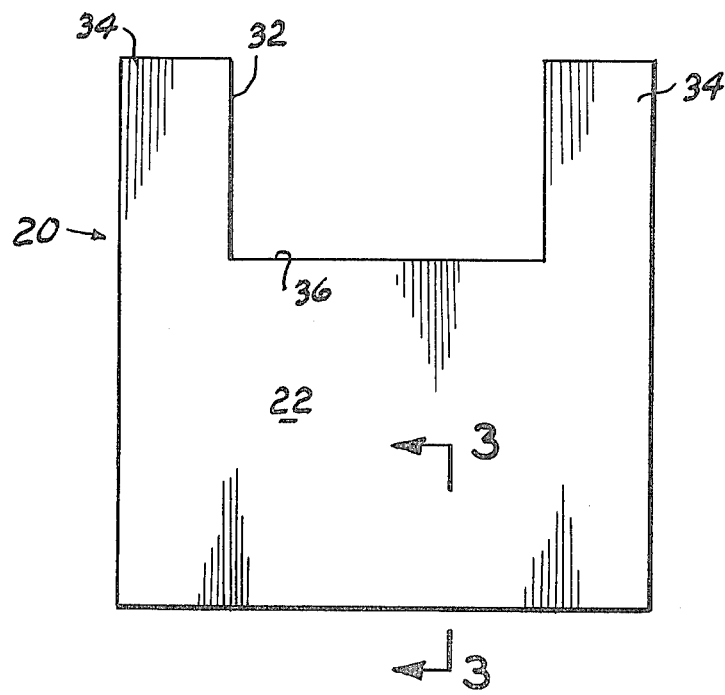
FIG. 2 is a plan view of the device, per se.

Like characters of reference designate like parts in those figures of the drawings in which they occur.

In the drawings:

The reference numeral 10 indicates a substantially conventional welder's face mask having an elongated front panel portion 12 integrally joined to side members 14, only one being shown, pivotally connected with headbands 16 for supporting the face mask forwardly of the welder's face and permitting vertical upward movement of the face mask to an out-of-the-way position. The panel 12 is provided with an opening covered by a lens 18 for shielding the welder's eyes from infrared and ultraviolet rays generated by the welding action. The above description of a face mask is set forth to show the combination with which the lung protector 20 is intended to be used.

Figure 3:
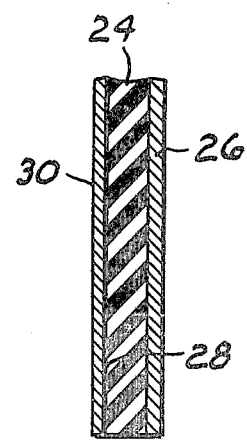
FIG. 3 is a fragmentary vertical cross sectional view taken substantially along the line 3—3 of FIG. 2.

The lung protector 20 comprises a substantially rectangular section of flexible sheet material 22 formed by a layer of rubber 24, or the like, having magnetic properties for attracting metallic particles, not shown, or provided on one of its flat surfaces with a layer of magnetic material 26. The opposite flat surface of the section 22 is provided with a layer of adhesive, indicated by the heavy line 28 (FIG. 3), having an overlying relatively thin peel-off backing 30 for maintaining the adhesive properties of the adhesive layer 28. The sheet material section 22 is preferably provided with a generally U-shaped opening 32 extending inwardly from one of its ends defining legs 34. Transversely the section 22 is preferably substantially coextensive with the width of the face panel 12. The length of the section 22, between the bottom of the U-shaped opening, defined by the line 36, and the opposite end of the section 22, is preferably coextensive with the spacing between the lens covered opening and the depending end of the face panel 12. The length of the leg portions 34 is preferably substantially equal to the vertical dimension of the lens covered opening.

OPERATION

In operation, the lung protector 20 is formed substantially as shown and described and is applied to the inner surface of the face mask panel 12 by peeling off the adhesive layer protective cover 30 and flatly applying the device 20 to the inner surface of the panel 12 with the adhesive layer 28 in contiguous contact therewith. Since the inner surface of the face mask panel 12, with the lung protector 20 attached thereto, is normally maintained during a welding action in close spaced relation with respect to the welder's nose and mouth, air drawn into the welder's lungs is substantially rendered clear of airborne metallic particles.

Obviously the invention is susceptible to changes or alterations without defeating its practicability. Therefore, I do not wish to be confined to the preferred embodiment shown in the drawings and described herein.

I claim:

1. In a welder's face mask including a panel portion vertically and horizontally at least coextensive with corresponding dimensions of a welder's face and provided with a welding light eye protective lens covered opening in its upward end portion and having an inner surface adjacent a welder's face when in use, the improvement comprising:

a layer of magnetic material bonded to the inner surface of said panel portion and extending upwardly from its depending end to at least the depending limit of the lens covered opening.

2. The combination according to claim 1 in which said layer comprises:

a section of flexible sheet material having magnetic material particles imbedded therein and having an adhesive coating on one of its flat surfaces, said adhesive coating adhesively joining said sheet material to said panel portion.

3. The combination according to claim 2 in which said section of sheet material encompasses at least three marginal edges of said lens covered opening.

* * * * *